United States Patent
Renirie et al.

[11] Patent Number: 6,110,098
[45] Date of Patent: Aug. 29, 2000

[54] SYSTEM AND METHOD OF MECHANICAL TREATMENT OF CARDIAC FIBRILLATION

[75] Inventors: Alexis Renirie, Berg en Dal; Vincent Schouten, Cadier en Keer; Koen Weijand, Hoensbroek, all of Netherlands

[73] Assignee: Medtronic, Inc., Minneapolis, Minn.

[21] Appl. No.: 08/769,070

[22] Filed: Dec. 18, 1996

[51] Int. Cl.⁷ .................................................. A61M 1/12
[52] U.S. Cl. ............................................ 600/16; 623/3
[58] Field of Search ................... 607/3–5; 623/3; 600/16, 17; 601/148–153

[56] References Cited

U.S. PATENT DOCUMENTS

| | | |
|---|---|---|
| 3,587,567 | 6/1971 | Schiff . |
| 4,265,228 | 5/1981 | Zoll . |
| 4,925,443 | 5/1990 | Heilman et al. . |
| 5,098,369 | 3/1992 | Heilman et al. . |
| 5,205,810 | 4/1993 | Guiraudon et al. ................. 600/16 |
| 5,383,840 | 1/1995 | Heilman et al. . |
| 5,433,731 | 7/1995 | Hoegnelid et al. . |

FOREIGN PATENT DOCUMENTS

| | | |
|---|---|---|
| 0 112 082 | 11/1983 | European Pat. Off. . |
| 2 288 741 | 11/1995 | United Kingdom . |
| WO 85/03634 | 8/1985 | WIPO . |
| WO 93/16652 | 9/1993 | WIPO . |

*Primary Examiner*—George R. Evanisko
*Attorney, Agent, or Firm*—Thomas F. Woods; Harold Patton; Michael J. Jaro

[57] ABSTRACT

There is provided an implanted system and method for delivering subsonic mechanical waves to one or more selected patient areas, the areas including the patient's heart and/or lungs. The mechanical waves are delivered for the purpose of treating fibrillation or like arrhythmias, for enhancing lung gas exchange, enhancing cardiac muscle fiber relaxation, and enhancing coronary perfusion. Mechanical waves are generated in a frequency range of about 1–100,000 Hz, and preferably 1–50,000 Hz. The waves may be delivered continuously for short or long time periods, or may be controlled in timing either with respect to detected portions of a patient's heartbeat signal or in response to a detected event such as fibrillation. In one preferred embodiment, the implantable system includes a defibrillation shock generator and control for responding to a defibrillation event by first delivering a sequence of mechanical waves and then delivering an electrical defibrillation shock. In another embodiment, the system and method treat incipient fibrillation or arrhythmia by delivering mechanical waves of predetermined timing to the patient's heart and/or lungs. In a specific embodiment, mechanical waves are delivered through an array of transducers to the patient's atrial wall, to treat atrial fibrillation.

3 Claims, 5 Drawing Sheets

SYSTEM AND METHOD OF MECHANICAL TREATMENT OF CARDIAC FIBRILLATION

FIELD OF THE INVENTION

The system and method of this invention relate to systems for treating cardiac fibrillation and, in particular, for using transducers driven at frequencies below the ultrasound range for mechanical treatment of the heart and related target areas.

BACKGROUND OF THE INVENTION

Delivery of electrical shocks has proven to be an effective and relatively safe means for defibrillation of the heart, or for treating various types of cardiac arrhythmias. Implantable defibrillators, cardioverters, and combined pacemaker/cardioverter/defibrillator devices have come into widespread use for treatment of various arrhythmias. As effective as these new devices and systems have been, there remain a number of areas where substantial development work is needed, in order to increase efficiency and reliability, and to deal with known adverse effects. Some of the known problem areas are those of tissue damage in the vicinity of the electrodes across which the shocks are delivered, and in the case of atrial defibrillation, the patient sensation of sharp pain which can be caused by over-stimulation of the phrenic nerve. Despite improvements in lead and electrode design, there remains an ongoing need to reduce the amount of energy delivered in a shock, both for purposes of preserving the battery energy in the implanted device and for the important purpose of reducing patient anxiety about receiving a shock.

One alternative approach to the area of defibrillation that has been considered but not given much development is using ultrasound for defibrillating. This involves delivering high energy ultrasound waves to the affected region, e.g., the atrium or ventricle. Unfortunately, this technique has thus far met with a low success rate, on the order of 30%, and has been seen to cause damage to the endothelium and to the cardiac muscle fibers. However, it is the basis of this invention that lower frequency mechanical agitation of the heart has a variety of potential beneficial effects which have not yet been successfully exploited, particularly in treating a fibrillating heart or a heart which is prone to fibrillation or other arrhythmias. Mechanical agitation of the heart, particularly at frequencies below about 50 kHz, can have a direct defibrillation effect, as well as other beneficial effects on the fibrillating heart. Mechanical agitation, or movement of the cardiac muscle with sufficient energy can change the conductive properties of the muscle, and thus change the loop gain and disrupt the circular conductive paths which had been responsible for the fibrillation or other arrhythmia. Likewise, mechanical agitation may affect action potential duration of myocardial cells, and thus aid in termination of fibrillation. Mechanical agitation directed to the cardiac muscle may facilitate muscle fiber relaxation, and help bring the fibers into diastole. This, in turn, can reduce the threshold for electrical defibrillation. Similarly, mechanical treatment may be used to improve cardiac perfusion. It is known that perfusion of the myocardium is limited to the diastolic phase, and that during fibrillation perfusion stops even though the aortic pressure remains high for a few seconds. Application of low frequency mechanical waves to the myocardium can have a relaxing effect which improves perfusion, as well as a direct massaging effect which aids perfusion.

In addition to direct mechanical treatment of the heart, mechanical vibration of the lungs may also be used to treat a fibrillation problem. Low frequency vibration is known to improve gas exchange in the lungs. Since oxygen supply and carbon dioxide are critical in a fibrillation condition, such mechanical vibration to provide enhanced gas exchange in the lungs is supportive of and beneficial to defibrillation. Further, depending upon the precise effects of the low frequency waves at the air-tissue interface in the lungs, such waves may have the property of stimulating the pulmonary stretch receptors. This will, via the cardio-pulmonary reflex, result in parasympathetic output (n.Vagus) in the heart and contribute to suppressing fibrillation. In view of these considerations, it is seen that there is substantial potential for therapeutic application of implantable low frequency mechanical wave devices for treating arrhythmias, particularly fibrillation and transient ischemic heart disease.

SUMMARY OF THE INVENTION

It is an overall object of this invention to provide a system and method for utilizing mechanical waves for treating a cardiac condition such as fibrillation by delivering the low frequency waves to at least a part of the patient's area comprising the heart and lungs, the mechanical wave treatment being utilized either alone or in combination with electric shock therapy.

In accordance with the above object, there is provided an implantable system and method for treating cardiac fibrillation and like conditions, involving delivery of mechanical waves to the patient's heart and/or lungs, the waves being in a frequency range of about 1–50,000 Hz and being generated by one or more transducers positioned within the patient's body for delivery of the waves to the target patient area. For example, the system may comprise a lead with a plurality of transducers adapted for positioning in the patient's atrium, and for mechanically treating the atrium. In another embodiment, the waves are directly transmitted to the outside surface of the patient's heart. Alternately, one or more wave transducers driven by the mechanical wave generator or generators may be positioned for delivering waves to the patient's lungs, or to portions of the lungs and the heart. The implantable system includes sensing electrodes for sensing the patient's natural cardiac activity, as well as cardiac responses to stimulation, and for controlling the wave treatments to be delivered at timed intervals with respect to the patient's cardiac signals and/or in timed relation to generated defibrillation or cardiac pulses delivered to the patient.

The invention thus embodies a system and method for providing mechanical treatment alone, or coordinating mechanical treatment of the patient's heart and/or lungs with defibrillation shock treatment delivered by a defibrillation pulse generator housed within the implanted system. The implanted system preferably has detection means for analyzing the patient history, detecting the timing and nature of arrhythmias, and for selecting an appropriate treatment in the form of a selected combination of mechanical wave treatment and defibrillation/cardioversion shock treatment.

DESCRIPTION OF THE PREFERRED EMBODIMENTS

Figure 1A:
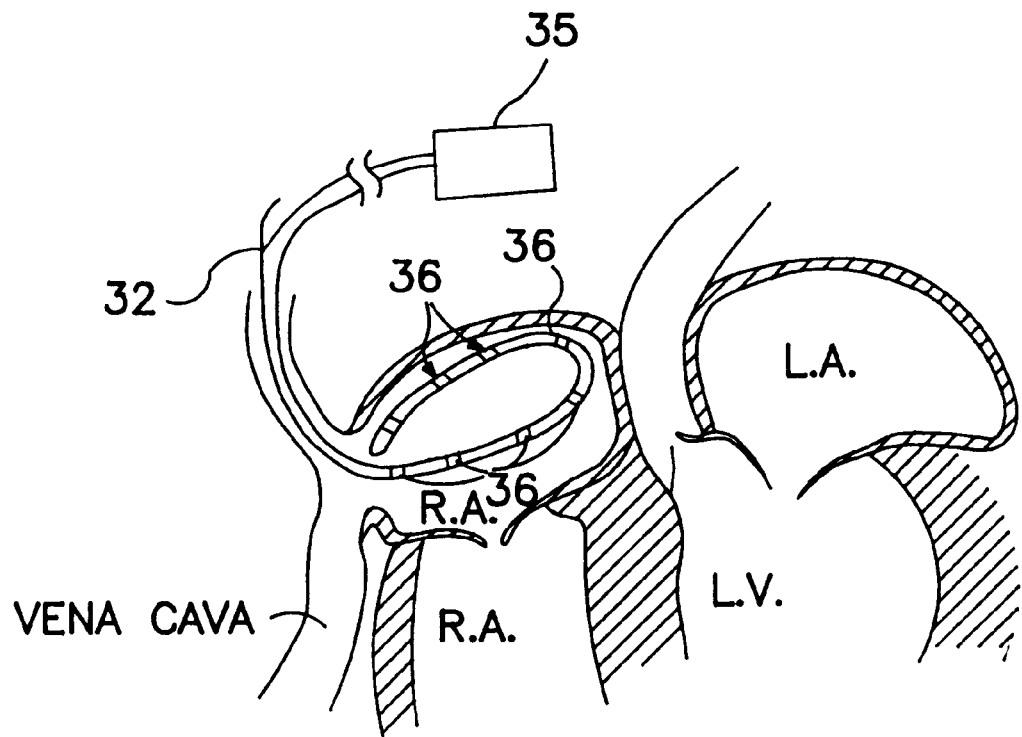
FIG. 1a is a schematic drawing showing an embodiment of an implantable lead for mechanical defibrillation and massage of a patient's atrium; the lead receives electrical signals at low frequencies from an implanted generator and delivers the signals to a plurality of crystal-type transducers positioned within or proximate to the atrial wall.

Referring now to FIG. 1a, there is shown a schematic diagram illustrating the placement of a lead 32 within the right atrium. The lead is connected to a signal generator 35 which suitably generates electrical signals programmable within a frequency range of 1–50,000 Hz, although higher frequencies up to about 100 kHz can be used within the scope of the invention. Different applications may suggest different frequencies. Thus, for cardiac relaxation applications, a useful range could be 10 to 200 Hz; for gas exchange applications, a desirable range may be 50–1000 Hz while for defibrillation applications, 50–10,000 Hz may be more suitable. It is expected that frequencies in the range of 50–100 kHz would not be very useful, but could be used in some applications. As used herein, the term "low frequency" refers to the preferred range of 1–50,000 Hz; the term "mechanical waves" refers to waves having frequencies up to 100 kHz.

The signals are connected from the generator to the proximal end of the lead 32, and conveyed through respective conductors (not shown) to transducers 36 which are arrayed along a distal length of the lead. Transducers 36 are conventional crystal-type transducers which provide mechanical movement in response to having electrical signals applied thereto. The transducer array may be varied with the application, and may be any desired plurality of transducers selected for the particular desired treatment. Alternately, the lead may use a smaller number of transducers, each having a greater individual length. Suitably the lead is positioned so that the transducers are close to as much of the atrial wall as possible. The lead is flexible and pre-shaped to take a position within the atrium, as illustrated; it is inserted into the right atrium through the jugular vein or another vein. Generator 35 is controllable with respect to the amplitude, duration and timing of the pulse signals applied to each of the respective transducers, as is discussed in more detail in connection with FIG. 4.

Figure 1B:
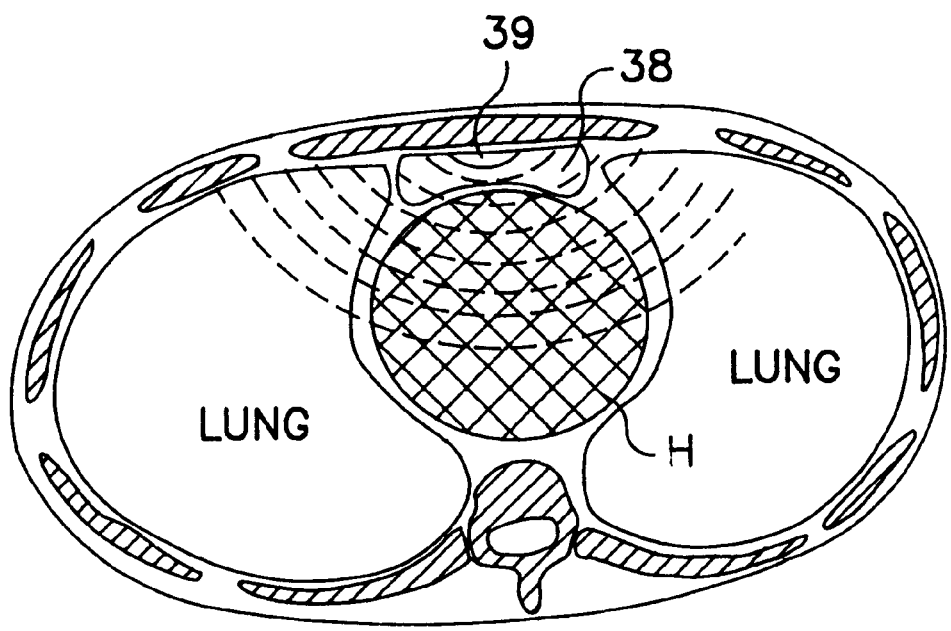
FIG. 1b is a schematic diagram illustrating a mechanical wave generator positioned in relation to the patient's lungs, for delivering mechanical waves to the lungs and to the air-tissue interface with the lungs.

Referring now to FIG. 1b, there is shown a schematic drawing of another embodiment of the invention, for delivering mechanical waves to the patient's heart as well as lungs. A fluid-filled pouch 38 is illustrated, which is a flexible diaphragm-type container inserted between the sternum and the pericardium of the patient's heart H. A vibration transducer 39 is positioned in the pouch, and connected through a lead (not shown) to a generator, such as generator 35. The pouch is positioned so that when electrical signals are applied to transducer 39, mechanical waves are generated which are conducted through the pouch to transmit to the heart as well as to the lungs. By placing the pouch against the sternum, there is provided means of pushing the waves into the heart. By this means the waves are effectively interfaced with the heart so as to shake and/or massage it. The effective interface is obtained by positioning the pouch so that there is essentially no space between pouch and the heart, i.e., the pouch is in direct contact with the heart across a significant surface area of the pericardium. The pouch may be designed to interface with one or both lungs, so as to deliver vibrations to them also.

Figure 2A:
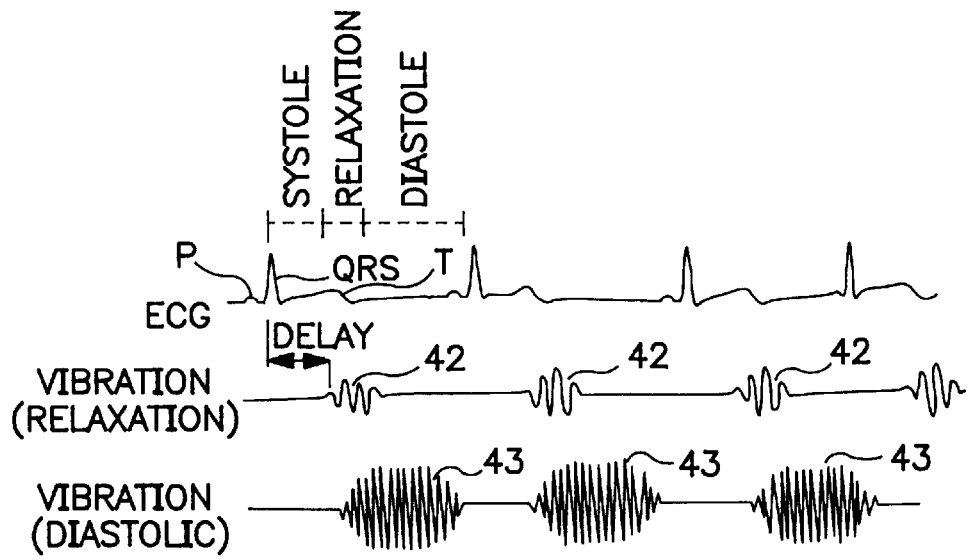
FIG. 2a presents a series of three curves, illustrating a normal sinus rhythm as seen on an ECG, and the timing of mechanical pulse groups delivered with respect to the systole (relaxation) and diastolic portions of a sinus period.

Referring now to FIG. 2a, there are shown timing diagrams illustrating a first application of the system of this invention. The top line shows a typical ECG representing a normal sinus rhythm. The P, QRS and T waves are indicated for this normal sinus. The systole interval is illustrated as being between the QRS and T wave. The cardiac relaxation period extends from the T waves for a short interval, during which the heart repolarizes; and the diastole interval follows until the next QRS wave. The second curve shows a series of relatively short low frequency burst signals 42, each positioned roughly within the relaxation period of each cardiac cycle. As discussed above, such mechanical agitation as produced by signals 42 is directed to achieve the effect of a more synchronous relaxation and repolarization of the cardiac muscle fibers, which may prevent arrhythmias and fibrillation. The third diagram shows a series of somewhat higher frequency and longer vibration signals 43, which are timed to be delivered during the diastolic period. Also discussed above, these diastolic signals are timed to aid in myocardial perfusion. The relief of ischemia may help to prevent arrhythmias and fibrillation.

Figure 2B:
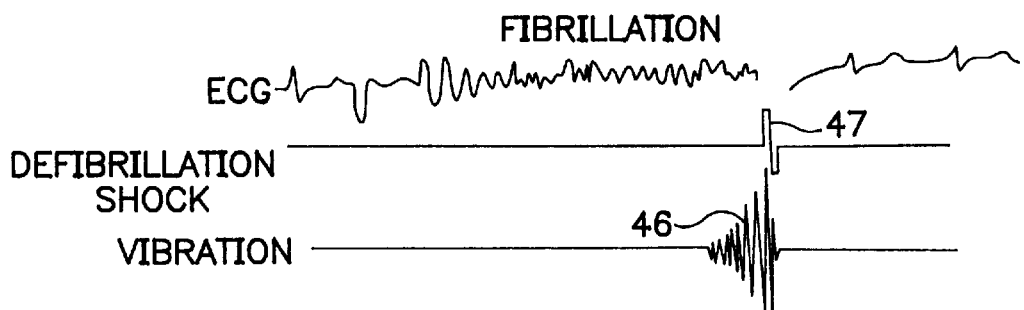
FIG. 2b illustrates three curves showing the timed relationship of a defibrillation shock and a vibration application with respect to each other in order to treat fibrillation.

Referring now to FIG. 2b, there are shown timing diagrams illustrating a defibrillation situation (top curve) and the synchronized delivery of a vibration signal 46 and a defibrillation shock 47. In this application, when cardiac fibrillation is sensed, and a decision to defibrillate is made, a vibration signal, or burst, as illustrated at 46, is first delivered to prepare the heart for the defibrillation shock 47, which is delivered substantially at the end of the mechanical vibration signal. Although the shock need not be delivered precisely at the end of the wave, it is important to coordinate the vibration and shock signals, to obtain the prior enhancement benefit of the vibration, enabling a lower amplitude defibrillation shock.

Figure 2C:
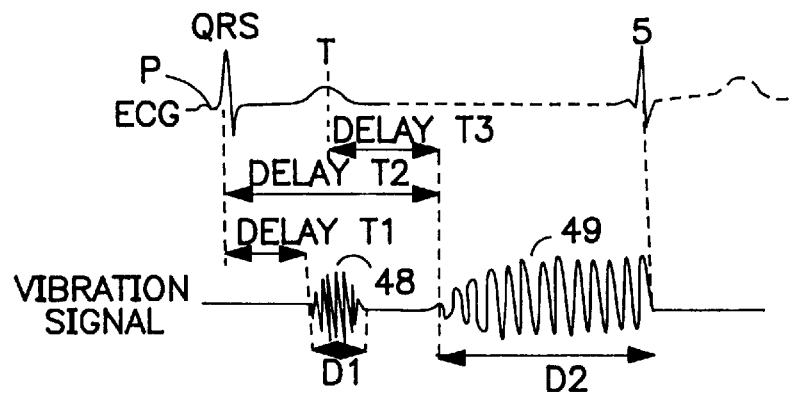
FIG. 2c illustrates two different types of vibration signal applications administered to a patient with first a normal sinus, and then a fibrillation condition respectively.

Referring now to FIG. 2c, there are shown two more timing diagrams comparing the timing of the vibration signals with patient cardiac activity. As shown in the top curve, the patient has a normal sinus rhythm, including the P wave, QRS and T wave; at some point, the patient is presumed to go into fibrillation. A delay T1, corresponding to the systole delay of FIG. 2a, can be timed out, at the end of which a mechanical signal 48 is applied having a duration D1, corresponding to the relaxation period; starting at the time of the QRS a second delay T2 is also timed out, at the close of which a second mechanical wave of duration D2 is generated and applied to the patient's heart, corresponding to diastole. Signals 48, 49 can be delivered continuously, and independent of any fibrillation, as long as the patient condition warrants. Thus, if ischemia is detected, these mechanical treatments are applied until the ischemia is no longer detected. Time T2 can be set to be of a length such that if no succeeding QRS is sensed and fibrillation is detected, then a defibrillation enhancing burst 49 is delivered. In this case, at the end of duration D2 an electrical shock S is delivered to terminate the fibrillation episode. In an alternate arrangement, the T wave is sensed, and a delay T3 is timed out; if there has been no further heartbeat, then the signal 49 is delivered.

Although FIG. 2c illustrates an application where the mechanical treatment is preliminary to electrical shock for disrupting fibrillation, it is to be noted that it is likewise within the invention to use direct mechanical shocks for treating a fibrillation condition. One or several short high energy mechanical shocks can be delivered to the heart, synchronized or not to a sensed patient cardiac signal. Thus, the invention embraces detection of fibrillation or other arrhythmia, followed directly by delivery of one or more mechanical shocks to the heart for defibrillation. The delivery of shocks can be made through the embodiments as illustrated in FIGS. 1a or 1b, or through other embodiments such as illustrated in FIGS. 3a, 3b and 3c to which reference is now made.

Figure 3A:
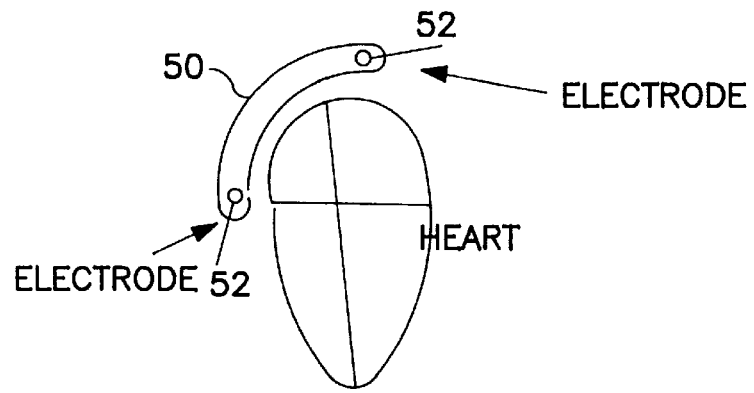
FIGS. 3a, 3b, and 3c are illustrations of arrangements for delivering mechanical shocks to a fibrillating heart to defibrillate it.
Figure 3B:
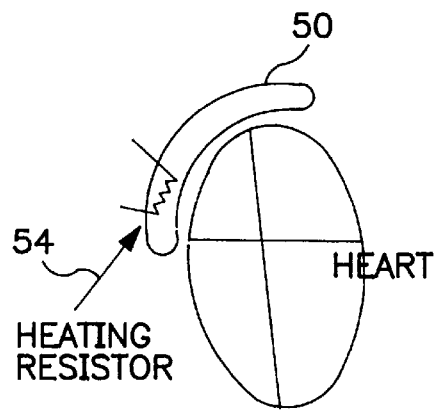
Figure 3C:
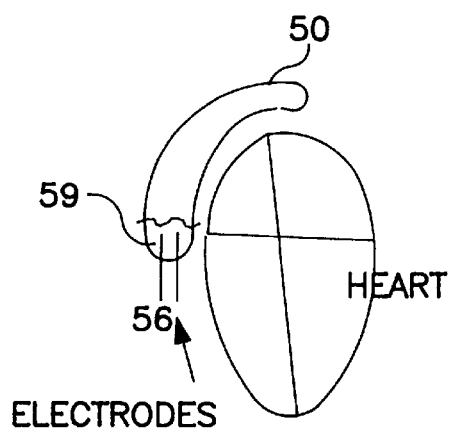

FIG. 3a shows a pouch 50 placed substantially in contact with the heart, which pouch is filled with water. A pair of electrodes 51, 52 deliver an electrical discharge into the fluid, causing a pulse-like mechanical wave to be transmitted to the heart. In FIG. 3b, the pouch is filled with water, and a heating resistor is used to quickly heat the water, creating a pressure wave. And in FIG. 3c, there is illustrated a pouch 50 which contains only a small amount of water shown at 55. When fibrillation is detected, current is applied through the electrodes 56 to hydrolyze the water; upon hydrolysis of all the water, a spark is ignited across the electrodes, which creates a shock wave of hydrogen and oxygen combustion, which wave is transmitted to the heart.

Figure 4:
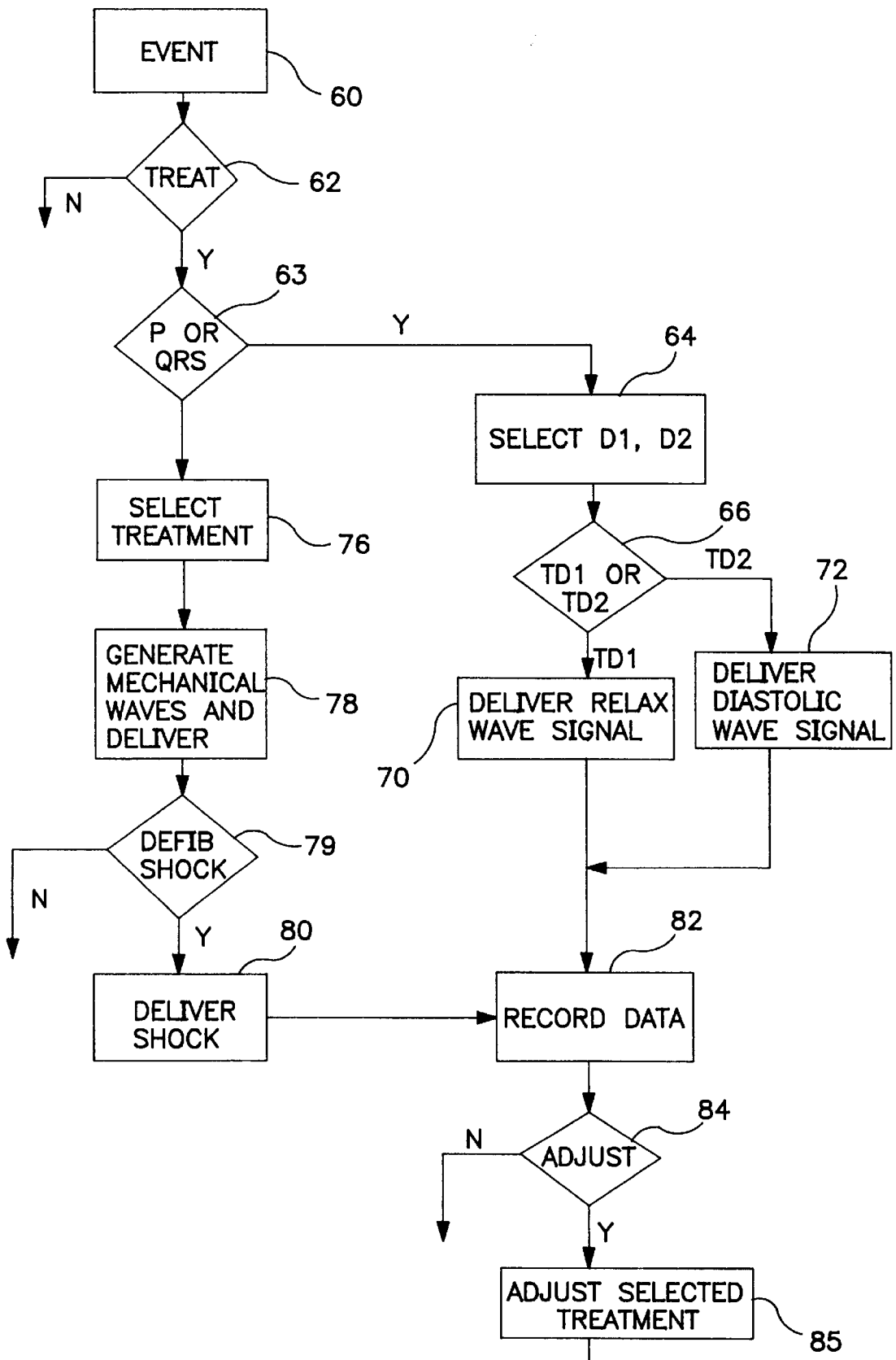
FIG. 4 is flow diagram representing the primary steps taken in applying mechanical defibrillation treatment in accordance with this invention, and specifically illustrates mechanical treatment which is coordinated with an electrical defibrillation shock.

Referring now to FIG. 4, there is shown a flow diagram of the primary steps taken in the method of treatment of this invention. The steps are taken automatically by an implantable device such as illustrated in FIG. 4. At block 60, it is determined whether an event has been sensed. In this context, an event may be a cardiac signal such as a P wave or a QRS wave; it may be a condition where no cardiac signal has been sensed for a period, such as would indicate fibrillation; or it may be a cumulative condition of high rates which would indicate an arrhythmia or fibrillation. At 62, it is determined whether a treatment involving application of mechanical waves is to be undertaken. If no, the routine exits; if yes, it goes on to 63 and determines whether the event has been a P or QRS wave. If yes, the routine branches to 64 and selects durations D1 and D2. Then at block 66 the D1, D2 durations are timed out, and at 68 the system looks for timeout of these two durations. When D1 has timed out, the routine goes to block 70, where a relax signal is generated and delivered, corresponding either to signal 42 in FIG. 2a or signal 48 in FIG. 2c. When D2 times out, the routine branches to block 72, where a diastolic signal is generated, corresponding to wave signal 43 in FIG. 2A.

Returning to 63, if the event is not a cardiac P or QRS wave, the routine goes to block 76 and selects the treatment to match the detected event. At 78, the selected signal is generated and delivered to the atrium or other selected target, for a predetermined period of time. For example, this signal can be the vibration signal 46 as illustrated in FIG. 2b, or the signal 49 as illustrated in FIG. 2c. Following this, at 79 it is determined whether a defibrillation or other cardioversion shock is to be delivered. If yes, and in timed relation to the mechanical signal, a defibrillation shock is delivered as indicated at block 80. The routine then records data concerning the event and the treatment at 82, and at 84 determines whether the treatment should be adjusted based on patient history. If no, the routine exits; if yes, the treatment is adjusted appropriately at block 85. For example, the amplitude or duration of the mechanical wave signal can be increased or decreased.

Figure 5:
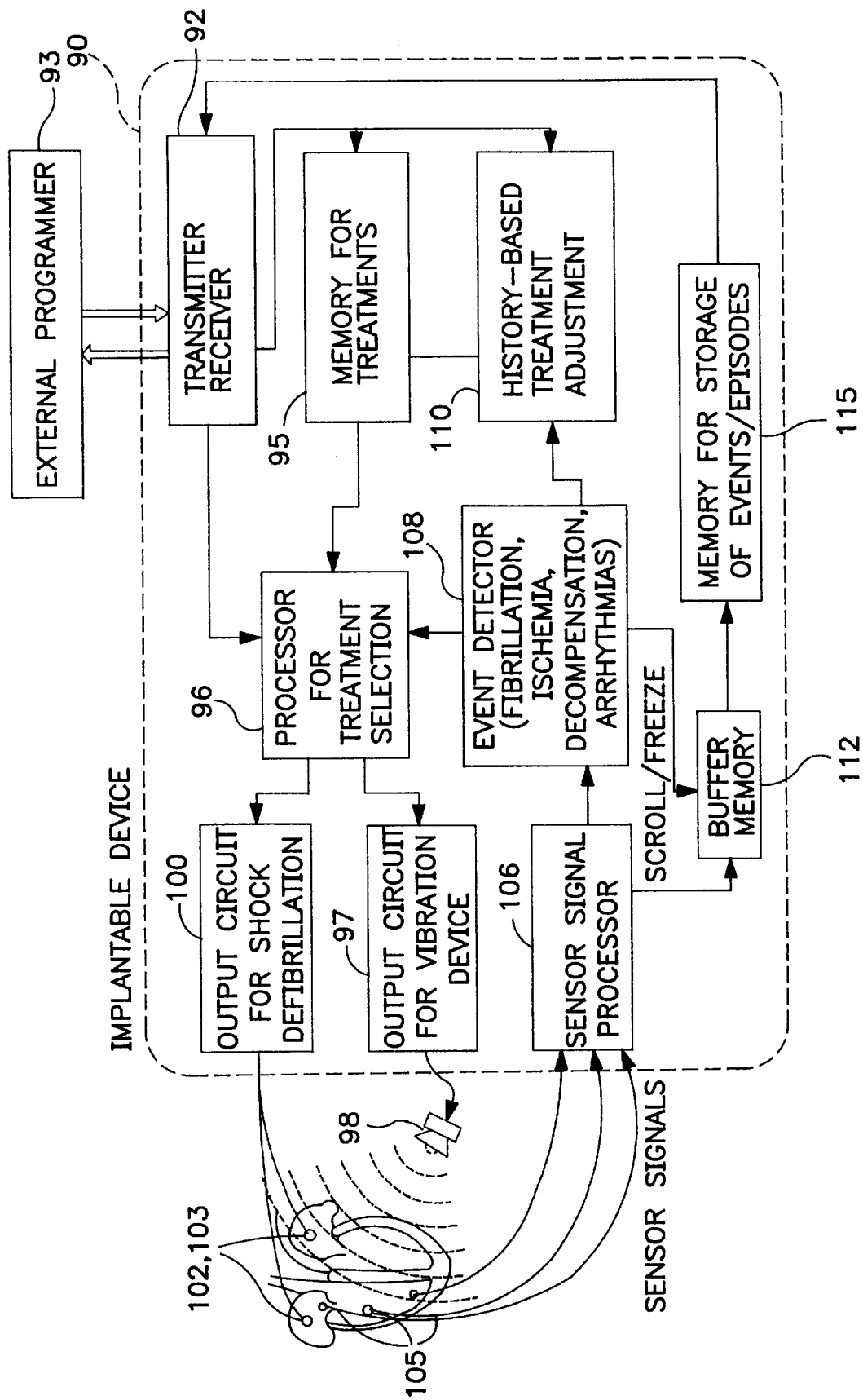
FIG. 5 is a system diagram showing the primary components of an implantable device for carrying out the system and method of this invention.

Referring now to FIG. 5, there is shown a block diagram of the primary functional components of an implantable device 90 in accordance with this invention. Device 90 may incorporate any appropriate technology, including a microprocessor and associated memory for software control of the illustrated functions. A transmitter receiver block 92 is in communication with an external programmer 93, for receiving programmed instructions and also for transmitting collected data for physician evaluation and use. A block 95 receives program data from transmitter receiver 92, and holds data in memory corresponding to respective treatments. Thus, this block may hold a number of different data groups for controlling the timing and sequence of mechanical and/or electrical signals. Block 96, which is suitably software control, constitutes a processor for treatment selection, and selects an appropriate treatment sequence corresponding to the evaluated patient condition. Block 96 provides output control signals to block 97, which is an output circuit for delivering electrical control signals to vibration transducer or transducer array 98, which is appropriately positioned in or proximate to the patient's heart. Output circuit 97 is suitably an electrical generator similar to that illustrated at 35 in FIG. 1a, and can be controlled in terms of the frequency of the output, the duration of the output, the amplitude of the output wave forms, and the timing of such wave forms. Transducer 98 may be a single transducer or an array of transducers, such as illustrated at 36 in FIG. 1a. Processor block 96 also provides electrical control signals to block 100, which is a conventional output circuit for generating and delivering defibrillation shock signals, as a standard in defibrillator systems. A defibrillator shock output from block 100 is connected through a lead to suitable electrodes on or within the patient's heart, illustrated at 102, 103. Of course, control 96 may control output 100 to deliver other types of cardioversion pulses.

Still referring to FIG. 5, sensor electrodes are illustrated at 105, for detecting cardiac responses at selected points in the patient's heart, illustrated here in the right atrium and right ventricle. The sensors are connected through a lead or leads to sensor signal processor 106, which provides conventional filtering and amplifying of the signals. The signals are connected to event detector 108, which provides known detection circuitry and/or software for detection of a patient condition, e.g., fibrillation, ischemia, decompensation, and various arrhythmias. Thus, event detector 108 provides the data for blocks 60 and 63 in FIG. 3. The output of event detector 108 is connected to processor 96, for making the determinations as to whether to treat, and the selection of the treatment, corresponding to blocks 62, 76 and 79 in FIG. 3. The events detected at 108 are also inputted to block 110, which provides for history-based treatment adjustment, which alters treatment memory data stored at block 95. Signals from 106 are also coupled to buffer memory 112, the data of which can be adjusted as a function of events detected at 108. The data from buffer memory 112 is coupled into memory 115 for storing event and episode data, which is then coupled to transmitter receiver 92 for transmitting to the external programmer device 93, where the patient data and history can be evaluated. As can be seen, as a function of this evaluation, new treatment data can be programmed into the implantable device.

There has thus been illustrated a system and method for providing improved cardiac therapy, and in particular improved mechanical treatment of fibrillation and other arrhythmias, with or without coordinated electrical shock treatment. Although the preferred embodiment concerns treatment which responds to detected events, the system and method is also applicable to prevention of fibrillation and other arrhythmias by application of mechanical waves to the patient's heart and/or lungs. In this regard, the implanted device can be programmed to deliver mechanical waves such as illustrated in FIG. 2a, without the occurrence of any fibrillation or other arrhythmia condition; or, the history-based treatment adjustment may select continuous mechanical treatment in order to prevent a fibrillation condition.

What is claimed is:

1. An implantable system for defibrillation of a heart of a patient, comprising:

implantable means for sensing fibrillation in an atrial chamber of the heart; and implantable mechanical means, operably connected to said sensing means, for generating and delivering at least one mechanical shock to said atrial chamber of the heart in response to sensed fibrillation.

2. The system as described in claim 1, wherein said mechanical means comprises means for delivering said mechanical shock to the outside of the heart.

3. The system as described in claim 1, wherein said mechanical means comprises pouch means for covering a part of epicardial surface of said heart, and burst means for causing a plurality of mechanical shocks to be generated within said pouch means.

* * * * *